United States Patent [19]

Leinert et al.

[11] 3,976,779
[45] Aug. 24, 1976

[54] 1,2,3,4-TETRAHYDRO-CARBAZOLE COMPOUNDS AND β-ADRENERGIC COMPOSITIONS

[75] Inventors: Herbert Leinert, Heppenheim; Alfred Popelak, Rimbach; Kurt Stach, Mannheim-Waldhof; Wolfgang Bartsch, Viernheim; Karl Dietmann, Mannheim-Vogelstang, all of Germany

[73] Assignee: Boehringer Mannheim G.m.b.H., Mannheim-Waldhof, Germany

[22] Filed: Apr. 16, 1975

[21] Appl. No.: 568,743

[30] Foreign Application Priority Data
May 21, 1974 Germany.............................. 2424523

[52] U.S. Cl................................. 424/274; 260/315
[51] Int. Cl.². ........................................ A61K 31/40
[58] Field of Search..................... 260/315; 424/274

[56] References Cited
UNITED STATES PATENTS

| | | | |
|---|---|---|---|
| 2,731,474 | 1/1956 | Long..................................... | 260/315 |
| 3,663,607 | 5/1972 | Barrett et al......................... | 260/315 |

*Primary Examiner*—Sherman D. Winters
*Attorney, Agent, or Firm*—Burgess, Dinklage & Sprung

[57] ABSTRACT

New 1,2,3,4-tetra-hydrocarbazole derivatives of the formula:

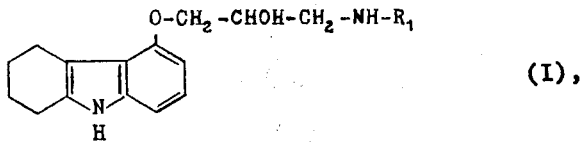

(I), wherein $R^1$ is straight-chained or branched alkyl, and the pharmacologically compatible salts thereof, are markedly effective as inhibitors of adrogenic β-receptors and thus useful for the treatment and prophylaxis of cardiac and circulatory diseases.

13 Claims, No Drawings

1,2,3,4-TETRAHYDRO-CARBAZOLE COMPOUNDS AND β-ADRENERGIC COMPOSITIONS

The present invention relates to novel 1,2,3,4-tetrahydrocarbazole compounds and to therapeutic compositions containing them. In addition, this invention is concerned with methods for the treatment, and prophylaxis of heart artery diseases.

The novel 1,2,3,4-tetra-hydrocarbazole compounds are of the formula:

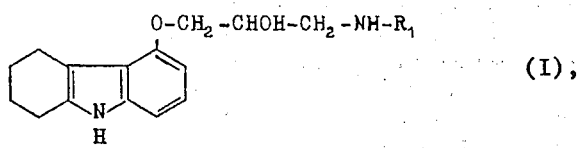

wherein $R^1$ is straight-chained or branched alkyl, and the pharmacologically compatible salts thereof. $R^1$ is preferably branched and can contain 1 to 8 carbon atoms, preferably 3 to 5 carbon atoms.

We have found that the new compounds block the activity of the β-receptors of the sympathetic nervous system and are therefore useful for the treatment and prophylaxis of heart artery diseases.

The process according to the instant invention for the preparation of the compounds of general formula (I) can be prepared, for example, by one of the following methods:

a. reaction of a compound of the formula:

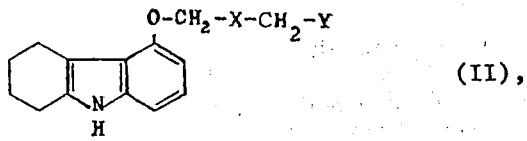

with a compound of the formula $$Z - R_3 \qquad (III),$$

wherein one of the radicals Y and Z is an amino group and the other one is a reactive radical and X represents the group $>C = O$ or $>CH-A$, wherein A can be a hydroxyl group or also together with Y, can be an oxygen atom, whereas $R_3$ has the same meaning as $R_1$ or represents a hydrogen atom, or b. a 1,2,3,4-tetrahydro-carbazole derivative of the formula:

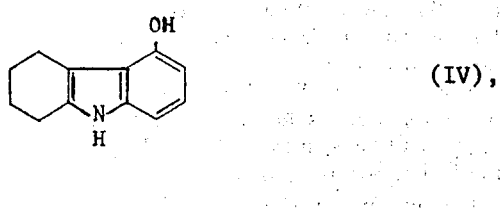

with a compound of the formula:

$$Y-CH_2-X-CH_2-NH-R_3 \qquad (V),$$

wherein Y, X and $R_3$ have the same meaning as above and, when X is a $>C = O$ group, the product obtained is subsequently reduced, whereafter — when $R_3$ is hydrogen — one alkylates subsequently and, if desired, converts the compounds of the general formula (I) thus obtained into a pharmacologically compatible salt.

The reactive groups Y and Z in the compounds of formulae (II), (III) and (V) are, in particular, acid residues, for example, of hydrohalic or sulfonic acids.

The reactions of formula (II) with compounds of formula (III) according to method (a), as well as of compounds of formula (IV) with compounds of formula (V) according to method (b), are preferably carried out in a polar solvent such as methanol, ethanol or dioxane. The reaction can also be carried out by mixing molar amounts of the reaction components and leaving the mixture to stand at ambient temperature. The reaction can be accelerated by heating briefly, if necessary, in the pressure vessel.

The reaction of the compounds of formula (IV) with the substances of the formula (V) according to method (b) is preferably carried out in the presence of an acid acceptor. However, an alkali metal salt of the hydroxy compounds of formula (IV) can also be used.

When it is necessary to carry out the reduction of a $>C = O$ group, this can be carried out by catalytic hydrogenation or by means of other appropriate reducing agents, for example, complex metal hydrides, such as sodium borohydride. Preferably, however, catalytic hydrogenation is employed using known catalysts, for example, noble metal catalysts or nickel catalysts in conventional solvents, for example, an alcohol or dioxane.

When it is necessary to carry out the subsequent N-alkylation in compounds of the formula (I) — in case that in the substances of formulae (III) and (V) used as starting compounds $R_3$ is hydrogen — the subsequent N-alkylation can be carried out in conventional manner, preferably with reactive alkyl compounds such as alkyl halogenides or dialkylsulfates. Preferably, the reactants are heated in an organic solvent such as ethanol, in presence of a base such as sodium or potassium carbonate. For the preparation of the compounds of formula (I) according to the instant invention, in which $R_1$ is a branched alkyl group, the alkylation of the amino group is preferably carried out by reaction with a suitable ketone under reducing conditions. Preferably, catalytic hydrogenation by use of Raney nickel or platinum metal catalysts is utilized. The hydrogenation is carried out in an inert solvent or in an excess of the ketone. The alkylation can also be carried out in presence of an alkali-borohydride with an excess of carbonyl compound. One works preferably at ambient temperature or at moderately elevated temperature.

The new compounds of formula (I) can be converted into their pharmacologically compatible salts by reaction, preferably in an organic solvent, with an equivalent amount of an inorganic or organic acid, for example, hydrochloric acid, hydrobromic acid, phosphoric acid, sulfuric acid, acetic acid, salicylic acid, citric acid, benzoic acid, naphthoic acid, O-acetoxybenzoic acid, adipinic acid or maleic acid.

The following examples ae given for the purpose of illustrating, without limiting, the preparation of the compounds used in the present invention:

EXAMPLE 1

Preparation of 1,2,3,4-tetrahydro-5-(2-hydroxy-3-tert. butylamino-propoxy)-carbazole 19 g 1,2,3,4-tetrahydro-5-(2,3-epoxy-propoxy)-carbazole were heated under reflux for 2 hours in a mixture of 100 ml ethanol and 50 ml tert. butylamine. The reaction mixture was then evaporated, the reaction residue dissolved in 150 ml ethyl acetate and the solution reacted with 10 ml glacial acetic acid, whereby the 1,2,3,4-tetrahydro-5-(2-hydroxy-3-tert. butylaminopropoxy)-carbazole hydroacetate crystallized out.

Yield: 24.1 g (= 95% of theory).

After recrystallization from methanol/ethyl acetate, the compound melts at 203°C.

The 1,2,3,4-tetrahydro-5-(2,3-epoxy-propoxy)-carbazole used as starting material was prepared in the following manner:

10.8 g 1,2,3,4-tetrahydro-5-hydroxy-carbazole were dissolved in 160 ml dioxane and mixed with 69.5 ml ln-soda lye and 45 ml epichlorhydrin solution and the reaction mixture stirred for 8 hours at 40°C. When the reaction was finished, the reaction mixture was diluted with 1.5 liter water and extracted four times with methylene chloride. The combined methylene chloride phases were dried over sodium sulfate and then evaporated. The residue was chromatographed for purification on an aluminum oxide column. (500 g neutral $Al_2O_3$; activity stage II; elution agent: toluene/methylene chloride 1:1).

After evaporating the column fractions, there were obtained 8.3 g of an oily residue which is sufficiently pure for the subsequent treatment.

EXAMPLE 2

Preparation of 1,2,3,4-tetrahydro-5-(2-hydroxy-3-isopropylamino-propoxy)-carbazole 8.3 g 1,2,3,4-tetrahydro-5-(2,3-epoxy-propoxy)-carbazole were heated under reflux for 7 hours in a mixture of 100 ml alcohol and 50 ml isopropylamine. The reaction mixture was then evaporated, the residue dissolved in toluene and chromatographed for purification over an aluminum oxide column (500 g basic $Al_2O_3$; Activity stage V; elution agent: toluene/methylene chloride 7:3).

After evaporating the column fractions, there was obtained an oily residue. The same was dissolved in isopropanol and the solution acidified with ethereal hyrochloric acid. The precipitated 1,2,3,4-tetrahydro-5-(2-hydroxy-3-isopropylamino-propoxy)-carbazole-hydrochloride was filtered off and recrystallized from a methanol/ethanol composition.

Yield: 5.2 g (= 45% of theory). Melting point 225°–226°C.

As noted above, the compounds of the instant invention have cardiac $\beta$-receptor blocking activity, and are therefore useful for the treatment and prophylaxis of cardiac and circulatory diseases.

The following tests were carried out to determine the toxicity and the cardiac $\beta$-receptor blocking activity of certain test compounds by determining the inhibition of the heart beat frequency increase induced by intravenous administration of isoprenalin.

The test compounds representative of the invention were the following:

Compound I: 1,2,3,4-Tetrahydro-5-(2-hydroxy-3-isopropylamino-propoxy)-carbazole

Compound II: 1,2,3,4-Tetrahydro-5-(2-hydroxy-3-tert. butylaminopropoxy)-carbazole As a comparison compound there was included:

Compound A: 1-Isopropylamino-3-(1-napthoxy)-2-propanol ("Propranolol")

These compounds were tested in the following manner:

The acute toxicity in mice when administered intravenously was measured and the $LD_{50}$ (=dosage at which 50% of the mice die) determined. The results were set forth in the table below.

The $\beta$-receptor blocking activity of the test compounds was tested on wake rabbits weighing between 2 to 3.5 kg. and kept in wooden cages. EKG-electrodes were inserted into the hind quarters of the rabbits s.c. (II. lead) and the heart frequency was measured based on 20 heart beats. The test compounds were then infused through a small tube to the ear vein of the rabbits over a period of 15 minutes. 30 minutes after the infusion isoprenalin (3,4-dihydro-a-[(isopropylamino)-methyl]-benzylalcohol) was injected intravenously at 1 /ug/kg.

The results are set forth in terms of inhibition of isoprenalin tachycardia, and are set forth in the table below:

TABLE

Blocking of Isoprenalin Tachycardia In Wake Rabbits

| Test Substance | Acute Toxicity $LD_{50}$ Mouse mg/kg i.v. | $DE_{250}*$ mg/kg i.v. | Therapeutic Index ($LD_{50}:DE_{250}$) |
|---|---|---|---|
| Control | — | | — |
| Comparison | | | |
| Compound A | 17 | 0.400 | 43 |
| Compound I | ~8 | 0.040 | ~200 |
| Compound II | 7 | 0.008 | 875 |

*Interpolated dosage which limits the frequency increase to 250 beats/min.

The above data show that the test compounds representative of the invention block tachycardia, depending on the administered dosage. The inventive compounds are already effective at dosages about 10 to 50 times smaller than the dosages required of the comparison compound in order to give the same tachycardia blocking effect.

Also, it will be seen that the inventive compounds provide a far greater margin of safety in that the margin between the dosage which is toxic to mice, and the dosage giving tachycardia blocking, is very large and substantially larger than the margin provided by the comparison compound. Thus the ratio of the $LD_{50}$ dosage to the dosage at which the test compounds limited the heartbeat frequency increase induced by isoprenalin to 250 beats per minute (as determined by interpolation and set forth in the table as $DE_{250}$ was many times greater for the inventive compounds.

The compounds according to the present invention are thus unexpectedly superior in effectiveness to known compounds and thus present a valuable contribution to the art.

The dosage of the novel compounds of the present invention depends on the age, weight, and condition of the patient being treated. Generally speaking, for aduloral administration, the preferred unit dosage of active compound with a suitable pharmaceutical diluent or lubricant is 1 mg. – 40 mg. four times a day. In general the oral dosage is 20 – 40 mg., whereas the intravenous dosage is generally 1 – 5 mg., four times a day.

For the preparation of pharmaceutical compositions, at least one of the new compounds according to the present invention is mixed with appropriate solid or liquid pharmaceutical diluents or carriers and, if desired, also with odoriferous, flavoring and coloring material and then formed into, for example, tablets or dragees or, with the addition of appropriate adjuvants, suspended or dissolved in water or oil, for example in olive oil.

The new compounds according to the present invention of general formula (I) and the salts thereof can be administered enterally or parentally in solid or liquid form. As injection medium, it is preferred to use water which contains the conventional additives for injection solutions, for example, stabilizing agents, solubilizing agents or buffers. Additives of this kind include, for example, tartrate and citrate buffers, ethanol, complex-forming agents (such as ethylenediamine-tetraacetic acid and the non-toxic salts thereof), and high molecular weight polymers (such as polyethylene oxide) for viscosity regulation. Solid carrier materials include, for example, starch, lactose, mannitol, methyl cellulose, talc, highly-dispersed silicic acids, high molecular weight fatty acids (such as stearic acid), gelatine, agaragar, calcium phosphate, magnesium stearate, animal and vegetable fats and solid high molecular weight polymers (such as polyethylene glycols); compositions which are suitable for oral administration can, if desired, contain flavoring and sweetening agents.

For preparing compounds such as tablets and other compressed formulations, the compounds can include any compatible and edible tableting material used in pharmaceutical practice as for example, corn starch, lactose, stearic acid, magnesium stearate, talc, methyl cellulose and the like.

Similarly the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral administration.

It will be appreciated that the instant specification and examples are set forth by way of illustration and not limitation, and that various modifications and changes may be made without departing from the spirit and scope of the present invention.

What is claimed is:

1. 1,2,3,4-Tetrahydro-carbazole compound of the formula:

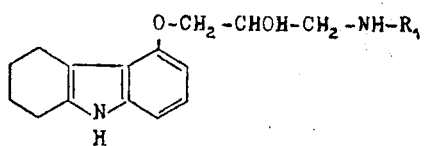

(I), wherein $R^1$ is straight-chained or branched alkyl of up to 8 carbon atoms, or a pharmacologically compatible salt thereof.

2. 1,2,3,4-Tetrahydro-carbazole compound as claimed in claim 1 wherein $R^1$ contains up to 5 carbon atoms.

3. 1,2,3,4-Tetrahydro-carbazole compound as claimed in claim 1 wherein $R^1$ contains 3 to 5 carbon atoms.

4. 1,2,3,4-Tetrahydro-carbazole compound as claimed in claim 1 wherein $R^1$ is branched.

5. 1,2,3,4-Tetrahydro-carbazole compound as claimed in claim 1 wherein $R^1$ is branched and contains from 3 to 5 carbon atoms.

6. 1,2,3,4-Tetrahydro-carbazole compound as claimed in claim 1 designated 1,2,3,4-Tetrahydro-5-(2-hydroxyl-3-tert. butylamino-propoxy)-carbazole.

7. 1,2,3,4-Tetrahydro-carbazole compound as claimed in claim 1 designated 1,2,3,4-tetrahydro-5-(2-hydroxyl-3-isopropylamino-propoxy)-carbazole.

8. Composition comprising a β-adrenergically effective amount of a 1,2,3,4-tetrahydro-carbazole compound as claimed in claim 1 in admixture with a pharmaceutically acceptable carrier.

9. Method of combating cardiac or circulatory insufficiency susceptible to treatment by β-adrenergic agents which method comprises administering to the subject a 1,2,3,4-Tetrahydro-carbazole compound of the formula:

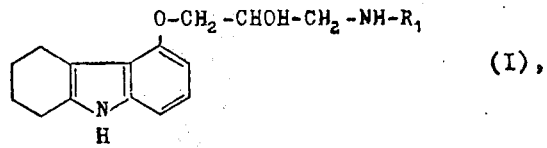

(I), wherein $R^1$ is straight-chained or branched alkyl of up to 8 carbon atoms or a pharmacologically compatible salt thereof.

10. Method as claimed in claim 9 wherein $R^1$ in the formula is branched alkyl of from 3 to 5 carbon atoms.

11. Method claimed in claim 9 wherein the said insufficiency is cardiac hypoxia.

12. Method as claimed in claim 9 wherein said compound is administered in a dosage of from 1 to 40 mg.

13. Method as claimed in claim 9 wherein said compound is at least one of the following:
   1,2,3,4-tetrahydro-5-(2-hydroxy-3-isopropylamino-propoxy)-carbazole and
   1,2,3,4-tetrahydro-5-(2-hydroxy-3-tert.butylamino-propoxy)-carbazole.

* * * * *